(12) United States Patent
Bombardelli

(10) Patent No.: US 11,534,472 B2
(45) Date of Patent: *Dec. 27, 2022

(54) COMPOSITIONS USEFUL IN THE PREVENTION AND/OR TREATMENT OF INFLAMMATION AND PAIN

(71) Applicant: Indena S.P.A., Milan (IT)

(72) Inventor: Ezio Bombardelli, Gropello Cairoli (IT)

(73) Assignee: INDENA S.P.A., Milan (IT)

(*) Notice: Subject to any disclaimer, the term of this patent is extended or adjusted under 35 U.S.C. 154(b) by 988 days.

This patent is subject to a terminal disclaimer.

(21) Appl. No.: 15/999,727

(22) PCT Filed: Feb. 20, 2017

(86) PCT No.: PCT/EP2017/053787
§ 371 (c)(1),
(2) Date: Aug. 20, 2018

(87) PCT Pub. No.: WO2017/144411
PCT Pub. Date: Aug. 31, 2017

(65) Prior Publication Data
US 2021/0205388 A1    Jul. 8, 2021

(30) Foreign Application Priority Data

Feb. 24, 2016 (IT) .................. 102016000019244

(51) Int. Cl.
| | |
|---|---|
| *A61K 36/28* | (2006.01) |
| *A61K 47/54* | (2017.01) |
| *A61P 29/00* | (2006.01) |
| *A61K 9/00* | (2006.01) |
| *A61K 31/12* | (2006.01) |
| *A61K 36/758* | (2006.01) |
| *A61K 36/9066* | (2006.01) |
| *A61K 36/9068* | (2006.01) |

(52) U.S. Cl.
CPC ............ *A61K 36/28* (2013.01); *A61K 9/0014* (2013.01); *A61K 31/12* (2013.01); *A61K 36/758* (2013.01); *A61K 36/9066* (2013.01); *A61K 36/9068* (2013.01); *A61K 47/548* (2017.08); *A61P 29/00* (2018.01)

(58) Field of Classification Search
None
See application file for complete search history.

(56) References Cited

U.S. PATENT DOCUMENTS 10,583,162 B2 * 3/2020 Bombardelli .......... A61K 31/16

FOREIGN PATENT DOCUMENTS

| CN | 1031315 A | 3/1989 | |
|---|---|---|---|
| CN | 103096907 A | 5/2013 | |
| CN | 104758451 A | 7/2015 | |
| WO | WO-0002570 A1 * | 1/2000 | ............ A61P 29/00 |
| WO | 2012013551 A1 | 2/2012 | |
| WO | 2015124616 A1 | 8/2015 | |

OTHER PUBLICATIONS

Belcaro (Alternative Medicine Review (2010), vol. 15, No. 4, pp. 337-344).*
Altman RD et al., "Effects of a ginger extract on knee pain in patients with osteoarthritis", Arthritis & Rheumatism, vol. 44, No. 11, Nov. 1, 2001, pp. 2531-2538.
Goetz P., "Phytotherapie de l'inflammation (partie I)", Phytotherapies; vol. 9, No. 5, Oct. 10, 2011, pp. 310-317.
International Preliminary Report on Patentability of PCT/EP2017/053787 dated May 9, 2018.
Search Report and Written Opinion of PCT/EP2017/053787 dated Apr. 7, 2017.
Communication of foreign associate dated Jan. 22, 2021 regarding office action received with regard to Chinese Patent Application No. 201780012244.3.
Nomura E.C.O. et al., "Antinociceptive effects of ethanolic extract from the flowers of Acmella oleracea (L.) R.K. Jansen in mice," Journal of Ethnopharmacology, Sep. 16, 2013, pp. 583-589.
Office Action issued by Chinese Patent Office dated Dec. 23, 2020 in counterpart patent application No. 201780012244.3.

* cited by examiner

*Primary Examiner* — Susan Hoffman
(74) *Attorney, Agent, or Firm* — Silvia Salvadori, P.C.; Silvia Salvadori

(57) ABSTRACT

Disclosed are compositions comprising: a) an extract of *Curcuma longa*, curcumin or phospholipid-complexed curcumin; b) a lipophilic extract of *Zingiber officinale*; and c) a lipophilic extract obtained from plants containing isobutylamides of polyunsaturated fatty acids selected from the group consisting of *Echinacea* spp. extract, *Zanthoxylum* spp. extract and *Acmella oleracea* (*Spilanthes oleracea*) extract.

4 Claims, No Drawings

COMPOSITIONS USEFUL IN THE PREVENTION AND/OR TREATMENT OF INFLAMMATION AND PAIN

This application is a U.S. national stage of PCT/EP2017/053787 filed on 20 Feb. 2017, which claims priority to and the benefit of Italian Application No. 102016000019244 filed on 24 Feb. 2016, the contents of which are incorporated herein by reference in their entireties.

TECHNICAL FIELD OF INVENTION

The present invention relates to compositions comprising an extract of *Curcuma longa*, curcumin or phospholipid-complexed curcumin; a lipophilic extract of *Zingiber officinale*; and a lipophilic extract obtained from plants containing isobutylamides of polyunsaturated fatty acids, which are useful in the prevention and/or treatment of inflammation and pain.

PRIOR ART

Peripheral inflammations, especially those associated with joint wear, osteoarthritis, rheumatoid arthritis and psoriatic arthritis, are among the main causes of disability in middle-aged and elderly persons.

Said disorders have very different etiologies. In some cases they are autoimmune disorders, and in others disorders due to mechanical wear on the main joints which undergo constant stress, especially when the individual is overweight.

Osteoarthritis (OA) is a degenerative disease characterised by synovial alterations and destruction of joint cartilage and subchondral bone. This condition affects and debilitates about 10% of the population between 65 and 73 years old.

Treatments for rheumatoid arthritis and psoriatic arthritis exist, although they are unpleasant and debilitating, while no specific treatment currently exists for osteoarthritis.

The first-line medicaments are still non-steroidal anti-inflammatory drugs (NSAIDs) with a symptomatic action, which are often poorly tolerated by patients.

The classic anti-inflammatories, from high-dose aspirin to those of the latest generation, necessarily involve lengthy treatments and serious side effects, especially at gastric level, and also, as recently discovered, at cardiac and vascular level.

This is one reason why the consumption of OA supplements has grown exponentially in recent years. Said supplements are substantially preparations based on chondroitin sulphate, glucosamine or hyaluronic acid, diacerein and unsaponifiable fractions of some oils, and are always used in combination with major drugs to reduce pain. All these products, and numerous other products of plant origin, are used, but one of the problems involved is their poor level of pain reduction, which forces patients to use the above-mentioned painkillers.

In the case of rheumatoid arthritis, which certainly constitutes the greatest cause of disability and loss of quality of life, and osteoarthritis, there is a need for new products which, while offering therapeutic efficacy, also provide better tolerability of the treatment.

Lipophilic extracts derived from medicinal plants, such as extracts of *Zingiber officinale, Echinacea* spp., *Zanthoxylum bungeanum, piperitum* or *armatum* and *Acmella oleracea*, are known to perform, on topical or systemic application, an anti-inflammatory and analgesic action associated with the presence of isobutylamides of unsaturated fatty acids, which are ligands of cannabinoid receptors CB1 and CB2 and vanilloids, and in particular act as TRPV1 agonists. Their anti-inflammatory activity is known to be modest compared with that of steroidal and non-steroidal anti-inflammatories.

*Curcuma longa* extracts are widely used in their countries of origin, and in the therapeutic context have been used to treat indigestion, flatulence, diarrhoea and joint pain. Many of these activities have been confirmed in vitro or in pharmacology, but little has been done at clinical level, where the data are contradictory. The active constituent of the plant is believed to be curcumin, which is currently undergoing numerous biochemical, pharmacological and clinical tests to identify its real activity, and hundreds of publications describe its potential benefits.

Preliminary clinical trials have demonstrated the very low systemic absorption of curcumin, partly due to the instability of the molecule at a physiological pH. Its low bioavailability does not allow any correlation with the in vitro tests (the plasma concentrations in humans are around 50 ng, including the secondary metabolites, after oral administration of 12 g).

WO2015/124616 describes compositions containing an extract of *Curcuma* spp., optionally as curcumin in the form of a complex with phospholipids, and an extract selected from *Echinacea* extract spp. and lipophilic extract of *Zanthoxylum* spp., for use in the topical and systemic treatment of peripheral pain and of superficial and deep inflammatory and painful states.

There is still a need to identify further alternative products which are useful in the prevention and/or treatment of inflammation and pain, especially osteoarticular inflammation and pain.

SUMMARY OF THE INVENTION

The present invention relates to compositions comprising:
a) an extract of *Curcuma longa*, curcumin or phospholipid-complexed curcumin;
b) a lipophilic extract of *Zingiber officinale*; and
c) a lipophilic extract obtained from plants containing isobutylamides of polyunsaturated fatty acids selected from the group consisting of *Echinacea* spp. extract, *Zanthoxylum* spp. extract and *Acmella oleracea* (*Spilanthes oleracea*) extract.

The present invention also relates to the use of said compositions in the prevention and/or treatment of inflammation and pain.

DETAILED DESCRIPTION OF THE INVENTION

It has surprisingly been found that compositions comprising an extract of *Curcuma longa*, curcumin or phospholipid-complexed curcumin; a lipophilic extract of *Zingiber officinale*; and an extract obtained from plants containing isobutylamides of polyunsaturated fatty acids, are effective in the prevention and/or treatment of inflammation and pain, especially osteoarticular inflammation and pain.

The present invention relates to compositions containing:
a) an extract of *Curcuma longa*, curcumin or phospholipid-complexed curcumin;
b) a lipophilic extract of *Zingiber officinale*; and
c) a lipophilic extract obtained from plants containing isobutylamides of polyunsaturated fatty acids selected from the group consisting of *Echinacea* spp. extract, *Zanthoxylum* spp. extract and *Acmella oleracea* (*Spilanthes oleracea*) extract.

According to a preferred aspect, the *Echinacea* spp. extract can be obtained from *Echinacea angustifolia* or *purpurea*; the *Zanthoxylum* spp. extract can be obtained from *Zanthoxylum bungeanum, Zanthoxylum piperitum* or *Zanthoxylum armatum*, and is preferably a *Zanthoxylum bungeanum* extract.

The *Curcuma longa* extract is preferably obtained from the tubers, and is more preferably an alcoholic extract.

The lipophilic extract of *Zingiber officinale* is preferably obtained from the roots and rhizomes. The extract also preferably has a high content of gingerols and shogaols, and a *Zingiber officinale* extract with a gingerols and shogaols content ranging from 20 to 30% w/w, preferably of 25% w/w, is particularly preferred.

*Echinacea* spp., *Zanthoxylum* spp. or *Acmella oleracea* (*Spilanthes oleracea*) extracts can be obtained by extraction with aprotic solvents from the fruit or parts of the respective plants normally used for extraction.

Lipophilic extracts of *Echinacea* spp., *Zanthoxylum* spp., *Zingiber officinale* and *Acmella oleracea* can be obtained by extraction from the roots or rhizomes with alcohols, ketones or aliphatic ethers or, preferably, with carbon dioxide under supercritical conditions according to EP0464298 A1 (page 2 lines 1-52, and page 5 line 45 to page 6 line 7). The lipophilic extract of *Zanthoxylum* spp. can be prepared in accordance with WO 00/02570 A1 (page 1 line 26 to page 2 line 13, and page 4 line 28 to page 7 line 21).

According to a preferred aspect of the invention, the compositions comprise:
a) phospholipid-complexed curcumin;
b) a lipophilic extract of *Zingiber officinale*; and
c) a lipophilic extract of *Echinacea* spp., *Zanthoxylum* spp. or *Acmella oleracea* (*Spilanthes oleracea*), preferably a *Zanthoxylum* spp. extract, and even more preferably a *Zanthoxylum bungeanum* extract.

The compositions according to the invention for oral administration can comprise, per unit dose:
a) phospholipid-complexed curcumin in amounts ranging from 50 to 1000 mg,
b) a lipophilic extract of *Zingiber officinale* in amounts ranging from 10 to 80 mg,
c) a lipophilic extract of *Zanthoxylum* spp. in amounts ranging from 1 to 50 mg or alternatively, a lipophilic extract of *Echinacea* spp. or *Acmella oleracea* (*Spilanthes oleracea*) in amounts ranging from 5 to 50 mg.

According to a particularly preferred aspect, the compositions for oral administration comprise 250 mg of phospholipid-complexed curcumin, 50 mg of lipophilic extract of *Zingiber officinale* and 10 mg of lipophilic extract of *Zanthoxylum* spp. per oral unit dose.

According to a further aspect, the compositions according to the invention for topical administration can comprise:
a) phospholipid-complexed curcumin in amounts ranging from 0.1 to 0.5 w/w,
b) a lipophilic extract of *Zingiber officinale* in an amount of 0.5% w/w, and
c) a lipophilic extract of *Zanthoxylum* spp. in amounts ranging from 0.1 to 1% w/w, preferably 0.5% w/w.

According to a particularly preferred aspect, the compositions for topical administration comprise 0.05% w/w of phospholipid-complexed curcumin, 0.5% w/w of lipophilic extract of *Zanthoxylum* spp. and 0.5% w/w of lipophilic extract of *Zingiber officinale*.

The present invention relates to compositions comprising:
a) an extract of *Curcuma longa*, curcumin or phospholipid-complexed curcumin;
b) a lipophilic extract of *Zingiber officinale*; and
c) a lipophilic extract obtained from plants containing isobutylamides of polyunsaturated fatty acids selected from the group consisting of *Echinacea* spp. extract, *Zanthoxylum* spp. extract and *Acmella oleracea* (*Spilanthes oleracea*) extract;

for use in the prevention and/or treatment of inflammation and pain.

The compositions according to the invention have proved useful in the prevention and/or treatment of peripheral pain of all kinds, such as diabetic neuropathy and muscle pain of different origins, and inflammatory states, such as skin inflammations of different origins.

The compositions have proved particularly effective in the treatment of osteoarticular inflammation and pain, e.g. peripheral and systemic pain, especially in the small and large joints.

The compositions according to the invention exhibit a potent analgesic and anti-inflammatory activity, greater than that found when the extracts are used separately, thus demonstrating a synergistic effect.

The ingredients of the composition according to the invention, when taken individually, exhibited modest efficacy, whereas when suitably combined they gave rise to a totally different profile in terms of tolerability and efficacy, exhibiting a synergic effect.

Formulations comprising the compositions according to the invention can be obtained by conventional techniques as described, for example, in "Remington's Pharmaceutical Handbook", Mack Publishing Co., N.Y., USA. In particular, the compositions according to the invention can be formulated by conventional formulation techniques used for plant ingredients, which require particular care to be taken to avoid interactions with the excipients and the capsule matrices.

The compositions according to the invention can be administered topically or orally.

Examples of oral formulations are tablets, dragées, soft and hard gelatin capsules, and cellulose capsules.

The compositions according to the invention can preferably be formulated in the form of soft capsules or emulsions.

The compositions according to the invention can be administered in combination with other products useful in the prevention and/or treatment of joint inflammation and pain.

The examples below further illustrate the invention.

EXAMPLES

Example 1

Soft gelatin capsules containing the following were prepared:

| | |
|---|---|
| Phospholipid-complexed curcumin | 200.00 mg |
| *Zingiber officinale* lipophilic extract (25% gingerols) | 50.00 mg |
| *Zanthoxylum bungeanum* extract extracted with $CO_2$ standardized to 25% in isobutylamides | 15.00 mg |
| Linseed oil | q.s. to 600 mg |

Example 2

Soft gelatin capsules containing the following were prepared:

| | |
|---|---|
| Phospholipid-complexed curcumin | 300.00 mg |
| Zanthoxylum piperitum extract extracted with $CO_2$ standardized to 25% in isobutylamides | 15.00 mg |
| Zingiber officinale extract (25% gingerols) | 50.00 mg |
| Linseed oil | q.s. to 700 mg |

Example 3—Test of In Vivo Activity in Laboratory Animal (Rat): Tail-Flick Test in the Rat The analgesic activity of a composition according to the invention comprising phospholipid-complexed curcumin, Zingiber officinale extract and Zanthoxylum bungeanum extract according to example 1 was compared with that of the individual ingredients administered separately in the rat and with that of a composition according to WO2015/124616 comprising phospholipid-complexed curcumin and a Zanthoxylum bungeanum extract in the same amounts of those used in the composition described in example 1 of the present invention.

The results demonstrated a clear synergy between the three ingredients of the compositions according to the invention, as shown in Table 1 below.

The analgesic activity was evaluated with the tail-flick test in the rat. Before treatment, three basic measurements were conducted on the animals to ensure that they were suitable for the handling and apparatus involved. The parameters used were 15V of radiant heat and a 15-second cut-off (to prevent irreversible harm to the animals), with evaluation of the tail-flick.

The animals were treated with 100 mg/Kg of the composition of example 1.

The same experimental model was used to evaluate the three individual ingredients of the composition, in three separate formulations, each containing one of the three active ingredients present in the composition described in example 1, in the same amount.

The control animals were treated with 0.1 ml of the oil used to dissolve the ingredients (carrier).

The analgesic effect was measured 15 and 30 min. after administration.

TABLE 1

| | | Latency time | | | |
|---|---|---|---|---|---|
| Treatment | Dose mg/Kg | after 15 min | % increase | after 30 min | % increase |
| Carrier | — | 4.1 ± 0.20 | — | 4.3 ± 0.35 | — |
| Composition described in example 1 | 100 | 13.6 ± 0.49 | 223.8 | 9.7 ± 0.13 | 125.6 |
| Zanthoxylum bungeanum lipophilic extract | 2.5 | 5.9 ± 0.26 | 43.9 | 5.1 ± 0.63 | 18.6 |
| Phospholipid-complexed curcumin | 33.3 | 4.2 ± 0.17 | 2.4 | 4.4 ± 0.43 | 2.3 |
| Zingiber officinale lipophilic extract (25% gingerols) | 8.3 | 4.3 ± 0.15 | 2.4 | 4.2 ± 0.21 | — |
| Composition according to WO2015/124616 | 100 | 9.8 ± 0.21 | 151.3 | 6.5 ± 0.22 | 58.5 |

Example 4 Evaluation of Analgesic Activity in Humans 40 patients suffering from knee joint disorders with constant pain were randomised and treated with two tablets a day according to example 1, one in the morning and one in the evening, or with placebo (consisting of the carrier alone).

Efficacy was scored on an international analogue pain scale with scores from 0 to 10, 10 points indicating maximum pain and 0 the disappearance of pain. The effect was evaluated on the second day after administration of the tablet, in the mornings 60 and 120 minutes after treatment.

The results are set out in Table 2 below.

TABLE 2

| | Pain (scores) at time | | |
|---|---|---|---|
| Treatment | 0 | 60 min. | 120 min. |
| Placebo | 9.3 ± 1.6 | 9.1 ± 1.2 | 8.9 ± 1.3 |
| Composition described in example 1 | 9.4 ± 1.9 | 4.7 ± 0.2 | 2.9 ± 1.6 |

Table 3 shows the results obtained, following treatment for up to three months with the composition according to the invention, on the global effect of osteoarthritis in patients recruited on the basis of the Karnofsky index (J. Clin. Oncology 1984; 2:187-193).

The evaluation was conducted by measuring the distance travelled without pain, and with different degrees of pain, on a treadmill set to 3 Km/h and an inclination of 10%. 80 patients suffering from osteoarthritis of the knee were divided into two groups. After randomisation, one group was treated with the placebo and the other with the composition described in example 1. During the treatment, pain was evaluated weekly with WOMAC, and the humoral parameters, which indicate the inflammatory parameters, were evaluated monthly, and they were found to have improved.

TABLE 3

| | Results of distance travelled on treadmill | | |
|---|---|---|---|
| | Distance travelled at time | | |
| Treatment | 0 | 1 month | 3 months |
| Placebo | 74.6 metres | 86.1 metres | xx |
| Composition described in example 1 | 75.1 metres | 165.6 metres | 355 metres | xx patients who left the trial for ethical reasons or were treated with other medicaments.

The combination of the oral and topical formulations proved effective in the clinical field, especially on patients suffering with knee joint disorders. The topical formulations proved particularly useful in the treatment of peripheral pain and of superficial and deep inflammatory and painful states. The combination can be applied directly to the skin in the oil wherein it is solubilised, or incorporated in creams or ointments suitable for administration. The treatment can be performed one to three times a day, applying a dose of 0.5-5 g of the topical formulation to the part of the body affected by the painful disorder.

The invention claimed is:
1. A composition comprising:
a) 200 mg of a phospholipid-complexed curcumin;

b) 50 mg of a lipophilic extract of *Zingiber officinale* containing 25% gingerols; and c) 15 mg of a lipophilic extract of *Zanthoxylum bungeanum*.

2. The composition according to claim 1, further comprising an extract of *Echinacea angustifolia* or *Echinacea purpurea*.

3. Method of preventing and/or treating inflammation and pain in patients in need thereof with the composition according to claim 1, said method comprising:

administering to said patients a pharmaceutically effective amount of the composition according to claim 1; and treating and/or preventing said inflammation and said pain in said patients.

4. The method according to claim 3, wherein the inflammation and pain are osteoarticular.

* * * * *